(12) United States Patent
Berg et al.

(10) Patent No.: US 8,728,828 B2
(45) Date of Patent: May 20, 2014

(54) PURIFICATION OF IMMUNOGLOBULINS

(75) Inventors: Hans Berg, Uppsala (SE); Hans Johansson, Uppsala (SE); Gunnar Malmquist, Uppsala (SE); Per-Mikael Aberg, Uppsala (SE)

(73) Assignee: GE Healthcare Bio-Sciences AB, Uppsala (SE)

( * ) Notice: Subject to any disclaimer, the term of this patent is extended or adjusted under 35 U.S.C. 154(b) by 1054 days.

(21) Appl. No.: 11/315,402

(22) Filed: Dec. 22, 2005

(65) Prior Publication Data

US 2006/0134805 A1 Jun. 22, 2006

(51) Int. Cl.
*G01N 33/543* (2006.01)

(52) U.S. Cl.
CPC .......... *G01N 33/543* (2013.01); *Y10S 436/824* (2013.01)
USPC ........... 436/518; 73/61.52; 210/656; 435/7.1; 436/501; 436/532; 436/824

(58) Field of Classification Search
USPC ............. 435/6, 7.1, 7.92–7.94; 436/501, 518, 436/523, 524, 529, 530; 73/61.52; 210/656–663; 530/387.1, 413
See application file for complete search history.

(56) References Cited

U.S. PATENT DOCUMENTS

| | | | | |
|---|---|---|---|---|
| 3,873,514 A | * | 3/1975 | Chu et al. | .......................... 536/3 |
| 4,444,879 A | * | 4/1984 | Foster et al. | .................. 435/7.95 |
| 5,089,605 A | * | 2/1992 | Profy et al. | ................. 530/388.1 |
| 5,151,350 A | | 9/1992 | Colbert et al. | |
| 5,153,844 A | | 10/1992 | Beni et al. | |
| 5,907,016 A | * | 5/1999 | Velander et al. | ............. 525/54.1 |
| 6,399,750 B1 | | 6/2002 | Johansson | |
| 6,428,707 B1 | * | 8/2002 | Berg et al. | ..................... 210/661 |
| 6,602,990 B1 | | 8/2003 | Berg | |

FOREIGN PATENT DOCUMENTS

| | | |
|---|---|---|
| JP | 09506067 A | 6/1997 |
| JP | 2000500649 A | 1/2000 |
| JP | 2000508361 A | 7/2000 |
| WO | WO 03/080655 | 10/2003 |

OTHER PUBLICATIONS

Grabski et al., Immobilization of Manganese Peroxidase from Lentiinula edodes and Its Biocatalytic Generation of Mn—Chelate as a Chemical Oxidant of Chlorophenols, Biotechnology and Bioengineering, vol. 60, No. 2, Oct. 20, 1998, pp. 204-215.*

Sofer, G., et al., "Handbook of Process Chromatography, A Guide to Optimization, Scale-Up and Validation", *Academic Press*, San Diego, 1997, p. 308-310.

Hermanson, G., et al., "Immmobilized Affinity Ligand Techniques", *Academic Press*, 1992, p. 118.

Hjertén, S., "The Preparation of Agarose Spheres for Chromatography of Molecules and Particles", *Biochimica et Biophysica Acta*, vol. 79, 1964, p. 393-398.

McCue, J., et al., "Evaluation of Protein-A Chromatography Media", *Journal of Chromatography A*, vol. 989, 2003, p. 139-153.

Porath, J., et al., "Thiophilic Adsorption—A New Method for Protein Fractionation", *FEBS Letters*, vol. 185, No. 2, 1985, p. 306-310.

Malmquist, G., et al., Design of a New Chromatography Base Matrix for Future Purification Scenarios: Optimisation of High Flow Agarose for Protein A Affinity Chromatography, Amersham Biosciences, 18-1155-90 Edition AA (2001).

Anonymous: "Protein A Agarose Kit Catalogue No. 553-50-00", Sep. 1, 2004, pp. 1-3, XP55014986, Gaithersburg, MD, Retrieved from the Internet: URL:http://web.archive.org/web/20040901150500/http:/www.kpl.com/docs/datasheet/5535000.PDF [retrieved on Dec. 15, 2011].

Anonymous: "MabSelect Xtra—Recombinant protein A-based, high-capacity affinity medium", Nov. 1, 2004, pp. 1-8, XP55015044, Uppsala, Retrieved from the Internet: URL:http://www.gelifesciences.co.jp/catalog/pdf/11001157.pdf [retrieved on Dec. 16, 2011].

Extended European Search Report issued Mar. 20, 2012 on corresponding EP patent application No. 05815565.6, Mar. 20, 2012.

Unofficial English translation of Office Action issued in connection with corresponding JP Application No. 2007-546603 on Jun. 28, 2011.

Unofficial English translation of Office Action issued in connection with corresponding JP Application No. 2007-546603 on Apr. 17, 2012.

Unofficial English translation of Office Action issued in connection with corresponding JP Application No. 2007-546603 on Mar. 12, 2013.

Affinity Chromatography, Principles & Methods, Pharmacia LKB Biotechnology, pp. 16-19, 1988.

* cited by examiner

*Primary Examiner* — Gary W Counts

(57) ABSTRACT

The present invention relates to a separation matrix comprised of porous particles to which antibody-binding protein ligands have been immobilized, wherein the ligand density is in the range of 5.0-10 mg/ml; the gel phase distribution coefficient of the particles expressed as $K_{av}$ for a dextran of size 110 kDa is above 0.65 and the median particle diameter is between 65-84 µm. The carbohydrate material is preferably highly cross-linked agarose.

21 Claims, 1 Drawing Sheet

PURIFICATION OF IMMUNOGLOBULINS

CROSS-REFERENCE TO RELATED APPLICATIONS

This application claims priority to U.S. provisional patent application No. 60/638,316 filed Dec. 22, 2004; the entire disclosure of which is incorporated herein by reference in its entirety.

FIELD OF THE INVENTION

The present invention relates to the field of antibody preparation, and more specifically to a separation matrix for isolation and/or separation of antibodies. The invention also encompasses a chromatography column that comprises the separation matrix of the invention, a method of isolating antibodies using said separation matrix and a multistep process for large-scale purification of antibodies from a crude feed.

BACKGROUND OF THE INVENTION

The immune system is composed of many interdependent cell types that collectively protect the body from bacterial, parasitic, fungal, viral infections and from the growth of tumour cells. The guards of the immune system are macrophages that continually roam the bloodstream of their host. When challenged by infection or immunisation, macrophages respond by engulfing invaders marked with foreign molecules known as antigens. This event, mediated by helper T cells, sets forth a complicated chain of responses that result in the stimulation of B-cells. These B-cells, in turn, produce proteins called antibodies, which bind to the foreign invader. The binding event between antibody and antigen marks the foreign invader for destruction via phagocytosis or activation of the complement system. Five different classes of antibodies, or immunoglobulins, exist: IgA, IgD, IgE, IgG, and IgM. They differ not only in their physiological roles but also in their structures. From a structural point of view, IgG antibodies are a particular class of immunoglobulins that have been extensively studied, perhaps because of the dominant role they play in a mature immune response.

The biological activity, which the immunoglobulins possess, is today exploited in a range of different applications in the human and veterinary diagnostic, health care and therapeutic sector. In fact, in the last few years, monoclonal antibodies and recombinant antibody constructs have become the largest class of proteins currently investigated in clinical trials and receiving FDA approval as therapeutics and diagnostics. Complementary to expression systems and production strategies, purification protocols are designed to obtain highly pure antibodies in a simple and cost-efficient manner.

Traditional methods for isolation of immunoglobulins are based on selective reversible precipitation of the protein fraction comprising the immunoglobulins while leaving other groups of proteins in solution. Typical precipitation agents being ethanol, polyethylene glycol, lyotropic i.e. anti-chaotropic salts such as ammonium sulphate and potassium phosphate, and caprylic acid. Typically, these precipitation methods are giving very impure products while at the same time being time consuming and laborious. Furthermore, the addition of the precipitating agent to the raw material makes it difficult to use the supernatant for other purposes and creates a disposal problem, which is particularly relevant when speaking of large-scale purification of immunoglobulins.

Ion exchange chromatography is a well-known method of protein fractionation frequently used for isolation of immunoglobulins. However, since the charged ion exchange ligands will react with all oppositely charged compounds, the selectivity of ion exchange chromatography may be somewhat lower than other chromatographic separations.

Hydrophobic interaction chromatography (HIC) is another method described for isolation of immunoglobulins. However, hydrophobic matrices require an addition of lyotropic salts to the raw material to make the immunoglobulin bind efficiently. The bound antibody is released from the matrix by lowering the concentration of lyotropic salt in a continuous or stepwise gradient. If a highly pure product is the object, it is recommended to combine the hydrophobic chromatography with a further step. Thus, a disadvantage of this procedure is the necessity to add lyotropic salt to the raw material as this gives and problem and thereby increased cost to the large-scale user. For other raw materials than cell culture supernatants such as whey, plasma, and egg yolk the addition of lyotropic salts to the raw materials would in many instances be prohibitive in large-scale applications as the salt could prevent any economically feasible use of the immunoglobulin depleted raw material. An additional problem in large-scale applications would be the disposal of several thousand liters of waste.

Thiophilic adsorption chromatography was introduced by J. Porath in 1985 (J. Porath et al.; FEBS Letters, vol. 185, p. 306, 1985) as a new chromatographic adsorption principle for isolation of immunoglobulins. In this paper, it is described how divinyl sulphone activated agarose coupled with various ligands comprising a free mercapto-group show specific binding of immunoglobulins in the presence of 0.5 M potassium sulphate, i.e. a lyotropic salt. Although the matrices described for thiophilic chromatography generally show good performance, since lyotropic salts are added to the raw material to ensure efficient binding of the immunoglobulin, disadvantages as discussed above will arise.

Affinity chromatography occupies a unique and powerful role in separation technology as the only technique that enables purification of a biomolecule on the basis of biological function or individual chemical structure. High selectivity and high capacity make this technique ideally suited for the isolation of a specific substance from complex biological mixtures. In affinity chromatography, the molecule to be purified is specifically and reversibly adsorbed by a ligand comprising a complementary binding substance covalently attached to an insoluble support. The sample is applied under conditions which favour its specific binding to the immobilized ligand. Unbound substances are washed away and the substance of interest can be recovered by changing the experimental conditions to those which favour its desorption. Affinity chromatography has a concentrating effect, which enables convenient processing of large sample volumes. Protein A and Protein G affinity chromatography are popular and widespread methods for isolation and purification of immunoglobulins, particularly for isolation of monoclonal antibodies, mainly due to the ease of use and the high purity obtained.

In 1982, Colbert et al. described a gene coding for a protein A-like material. In U.S. Pat. No. 5,151,350, the successful cloning and expression of such genes was described for the first time. The cloning of this gene with its nucleotide sequence characterisation enables those skilled in the art to obtain quantities of a protein A-like material nucleotide sequence for cloning in various host-vector systems. Such recombinantly produced protein A-like material, and subfragments thereof, have the protein A properties of binding to IgG at the Fc region and activation of polyclonal antibody synthesis. Thus, these entities are useful in chromatography in the same manner as protein A. In the pharmaceutical industry, an obvious advantage of the recombinant protein A chromatography is that the risk of mammalian residues in the separation matrix, and consequently the risk of mammalian traces in the pharmaceutical product, has been eliminated.

U.S. Pat. No. 6,399,750 discloses an IgG-binding medium, and more specifically a separation medium having a base matrix and matrix-bound groups which exhibit recombinant Protein A (rProtein A) containing a cysteine. The groups are of formula: —B—X-rProtein A, wherein B is a bridge which binds to the base matrix and X includes a heteroatom N or S from rProtein. In a preferred embodiment X is a thioether sulphur originating which also constitutes the C-terminal residue is the cysteine of rProtein A.

Various Protein A chromatography products are available on the market. For example, Millipore (Billerca, Mass., USA) offers both Prosep-A High Capacity, made with natural protein A derived from *Staphylococcus aureus* and PROSEP-rA High Capacity, manufactured using recombinant protein A expressed in *Escherichia coli*. The PROSEP matrix consists of glass particles permeated by interconnecting pores.

McCue et al. (Journal of Chromatography A, 989 (2003) 139-153: "Evaluation of protein A chromatography media") studied two protein A media of different pore sizes, both having porous glass backbones. A larger static capacity was found for the smaller pore size material, which is suggested to result from the larger specific surface area and associated higher ligand concentration. A larger dynamic binding capacity was also found for the smaller pore size material.

MabSelect™ is a Protein A chromatography product available from Amersham Biosciences (Uppsala, Sweden) especially suitable for capture of monoclonal antibodies from large volumes of feed. The ligands comprise recombinant Protein A coupled to a cross-linked agarose support via a C-terminal cysteine. The median particle diameter of MabSelect™ is 85 μm.

However, despite the state of the art constructions, there is still a need of alternative separation matrices for purification of antibodies or antibody constructs, which observe the demands of purity, safety, potency and cost effectiveness.

BRIEF DESCRIPTION OF THE INVENTION

One aspect of the present invention is a novel separation matrix suitable for purification of polyclonal or monoclonal antibodies. This can be achieved as defined in the claims. Another aspect of the invention is a separation matrix which allows faster and more economic purification of antibodies than the prior art. This can be achieved by a novel separation matrix as defined in the appended claims, which enables a substantially increased binding capacity when used in chromatography.

A further aspect of the invention is a separation matrix as described above, which is suitable for large scale operation. A more specific aspect is such a separation matrix, which enables substantially increased binding capacity from a crude feed.

An additional aspect of the invention is a chromatography column packed or filled with a separation matrix according to the invention.

Yet a further aspect is a kit which comprises a chromatography column according to the invention, buffer suitable for antibody purification and written instructions.

One more aspect is a method of isolating antibodies from a liquid using a separation matrix according to the invention. The separation matrix may be provided in a separation column according to the invention. The method according to the invention is useful either to obtain a specific antibody species in substantially pure form, or to obtain a liquid from which one or more undesired antibodies have been removed.

Further embodiments and advantages of the present invention will appear from the appended claims and the description below.

DEFINITIONS

Figure 1:
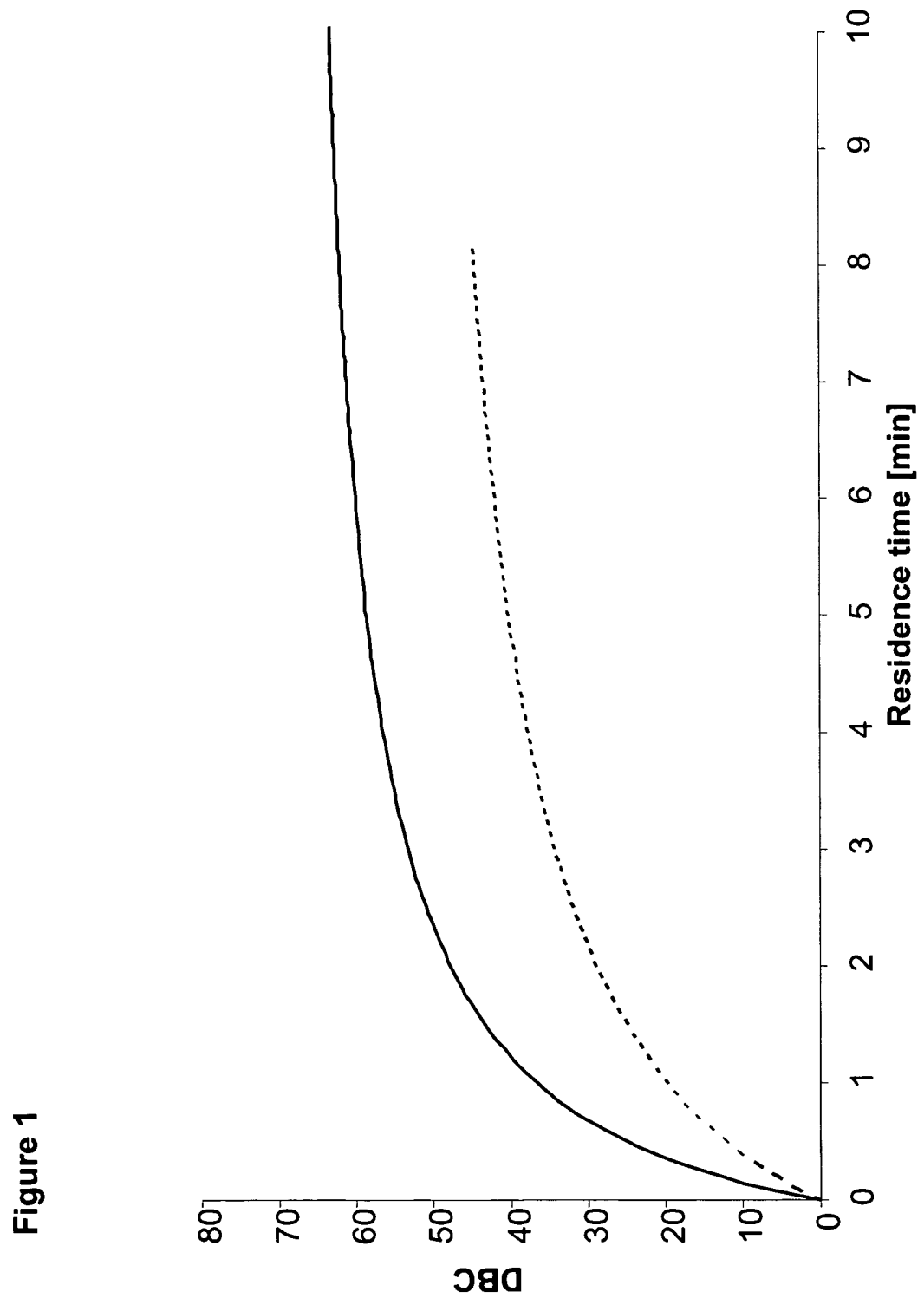
FIG. 1 is a diagram wherein the dynamic binding capacity (DBC) (mg antibody/ml separation matrix) is shown on the Y axis, as a function of residence time (minutes) on the X axis, for a separation matrix according to the invention (upper line) and for a prior art product (lower dotted line). It appears clearly how the separation matrix according to the invention provides a substantially higher, in fact, about 30% higher, dynamic binding capacity.

The terms "antibody" and "immunoglobulin" are used herein interchangeably.

The term "ligand" means herein molecules or compounds capable of interaction with target compounds, such as antibodies.

The term "spacer arm" or "bridge" means herein an element that distances a ligand from the support of a separation matrix. The support of the separation matrix is also known as the "base matrix", while the term "separation matrix" as used herein is also known as a separation media.

The term "antibody-binding protein" means herein a protein capable of binding antibodies, regardless of binding mechanism.

The term an "Fc-binding protein" means a protein capable of binding to the crystallisable part (Fc) of an antibody and includes e.g. Protein A and Protein G, or any fragment or genetic derivative or fusion protein thereof that has maintained said binding property.

The term "eluent" is used in its conventional meaning in this field, i.e. a buffer of suitable pH and/or ionic strength to release one or more compounds from a separation matrix.

The term $K_{av}$ refers to the gel phase distribution coefficient, which is a column independent variable calculated from the elution, or retention volume, $V_R$ (also denoted $V_e$) for a molecule of a given size, the interstitial void volume, $V_0$, and the geometric volume of the column ($V_c$) according to $K_{av}=(V_R-V_0)/(V_c-V_0)$ (see e.g. "Handbook of Process Chromatography, A Guide to Optimization, Scale-Up and validation" (1997) Academic Press, San Diego. Gail Sofer & Lars Hagel eds. ISBN 0-12-654266-X, p. 368).

DETAILED DESCRIPTION OF THE PRESENT INVENTION

In a first aspect, the present invention relates to a separation matrix comprised of porous particles to which antibody-binding protein ligands have been immobilised, wherein the gel phase distribution coefficient of the base matrix expressed as $K_{av}$ for a dextran of size 110 kDa is above 0.65 and the median particle diameter is between 65 and 84 μm. In one embodiment, the present invention relates to a separation matrix comprised of porous particles to which antibody-binding protein ligands have been immobilised, wherein the ligand density is in the range of 5.0-10 and the median particle diameter is between 65 and 84 μm. In another embodiment, the present invention relates to a separation matrix comprised of porous particles to which antibody-binding protein ligands have been immobilised, wherein the ligand density is in the range of 5.0-10 mg/ml; the gel phase distribution coefficient of the base matrix expressed as $K_{av}$ for a dextran of size 110 kDa is above 0.65 and the median particle diameter is between 65 and 84 μm.

In one embodiment, the ligands of the present separation matrix comprise antibody-binding protein, such as Protein A, G and/or L. In one embodiment, the ligands comprise Fc-binding protein. In the most advantageous embodiment, the Fc-binding protein is Protein A. In a preferred embodiment, the ligands comprise recombinant Protein A produced in a non-mammalian source. In this context, it is understood that the phrase "comprising" Protein A should be interpreted as comprising Protein A or a functional equivalent thereof, which has retained the Protein A IgG-binding properties. The recombinant Protein A ligands may be coupled to the particles via single or multiple attachments, preferably via cysteine. In an alternative embodiment, the ligands comprise κ-binding protein, such as Protein L.

In a specific embodiment, the ligands of the present separation matrix comprise a monomer, dimer or multimer of Protein A domains. Thus, the ligands may comprise one or more of Domain A, B, C, D and E, preferably Domain B and/or Domain C. In a specific embodiment, such a dimer or multimer comprises Protein Z, which is a mutated form of Domain B, see e.g. U.S. Pat. No. 5,143,844 (Abrahamsen et al.). In an advantageous embodiment, which facilitates cleaning in place (CIP) while maintaining the excellent binding capacity obtained according to the invention, the ligands comprises one or more alkali-stable Protein A domains. Thus, in this embodiment, the ligands comprise mutated protein, wherein one or more of said Protein A domains have been mutated, see e.g. WO 03/080655 (Amersham Biosciences), which is hereby incorporated herein via reference. In an alternative embodiment, the ligands comprise one or more of Domain C from Protein A. The separation matrix comprising alkali-stable monomeric or multimeric ligands are easily prepared by the skilled person in this field e.g. as described in WO 03/080655 (Amersham Biosciences).

In an alternative embodiment, the present ligands are antibody-binding peptides. Thus, the separation matrix according to this embodiment is comprised of porous particles to which antibody-binding protein ligands have been immobilised, wherein the gel phase distribution coefficient of the base matrix expressed as $K_{av}$ for a dextran of size 110 kDa is above 0.65 and the median particle diameter is between 65 and 84 μm.

The present base matrix may comprise porous particles made from any material within the specified values of the gel phase distribution coefficient, which provides the substantial improvement of dynamic binding capacity (DBC) described herein. In an advantageous embodiment of the present invention, the particles, i.e. the support of the separation matrix, are made from a cross-linked carbohydrate material, such as agarose, agar, cellulose, dextran, chitosan, konjac, carrageenan, gellan, alginate etc, which are easily prepared according to standard methods, such as inverse suspension gelation (S Hjertén: Biochim Biophys Acta 79(2), 393-398 (1964). In one embodiment, the carbohydrate material is highly cross-linked agarose, such as Sepharose™ (Amersham Biosciences, Uppsala, Sweden).

In a preferred embodiment of the present invention, the support is a porous cross-linked agarose material that exhibits advantageous mechanical properties and consequently allows high flows without developing too high a pressure. In this embodiment, the agarose polymers have been allylated before gelation. Such agarose particles are advantageously prepared as described in U.S. Pat. No. 6,602,990 (Amersham Biosciences, Uppsala, Sweden), which is hereby incorporated herein via reference. In brief, a bifunctional cross-linking agent, having one active site and one inactive site, is introduced into the agarose solution before gel formation. and allowed to react with the hydroxyl groups of the agarose whereby it is chemically bound to the agarose. In the first step of the process a solution or dispersion of the polysaccharide is formed. A gel is then formed of the polysaccharide by emulsifying the water solution in an organic solvent, after which the inactive site of the cross-linking agent is activated and reacted with hydroxyl groups of the polysaccharide. After this initial cross-linking, further cross-linking can be carried out by conventional methods.

The particles of the present separation matrix are polydisperse, and may be defined by a particle diameter within a range of 30-140 μm, preferably 43-128 μm and more preferably 70-84 μm. Another commonly used way of defining particle size within this field is the median particle diameter of the cumulative volume distribution, which for the present separation matrix is in the range of 65-84 μm, such as about 75 μm. In an alternative embodiment, the present particles are monodisperse and defined by a particle diameter of 74-76 μm, such as 75 μm. As is well known in this field, the particle size is easily controlled during the process by withdrawing a sample of the emulsion, estimating the particle diameter under microscope and subsequently adjusting the stirring to decrease the particle size.

The ligands may be immobilised to the particles according to the invention using any well known method, such as epoxi coupling. In a specific embodiment, the ligand density is in the range of 5-10 mg/ml. The density i.e. concentration of immobilised ligands is easily controlled by the skilled person in this field, see e.g. Hermanson, Greg T., Mallia, A. Krishna, Smith, Paul K. Immobilized Affinity Ligand Techniques, p. 118. Academic Press. ISBN 0-12-342330-9. Specific methods of immobilisation of Protein A, such as recombinant Protein A, are also described in the literature.

Thus, in one embodiment of the present separation matrix, the gel phase distribution coefficient of the particles expressed as $K_{av}$ for a dextran of size 110 kDa is above 0.60, and preferably above 0.65. Thus, in one embodiment, the gel phase distribution coefficient of the particles expressed as $K_{av}$ for a dextran of size 110 kDa is in the range of 0.60-0.90, preferably 0.65-0.85 and more preferably in the range of 0.65-0.75. The gel phase distribution coefficient of such a support is easily controlled by the skilled person in this field by adjustment of the solids content. The reason for using the $K_{av}$ value rather than exact values of pore diameter or the like is that for a hydrogel like agarose, exact measurement of pore diameters are difficult in a wet state and pore sizes estimated after drying of the hydrogel do not truly reflect the wet state.

The dynamic binding capacity of a separation matrix is a good indication of the suitability of a separation matrix for large scale operation, where process economy is greatly improved by such an increase. In one embodiment, the present invention is a separation matrix that provides a dynamic binding capacity above 40 mg antibody/ml separation matrix at 2.4 minutes residence time. In a specific embodiment, the separation matrix provides a dynamic binding capacity above 35 mg/ml, e.g. in the range of 35-50, such as about 39-40 mg/ml separation matrix.

Thus, if the present separation matrix is compared to prior art such as the MabSelect™ product discussed above, the invention presents an increase of the gel phase distribution coefficient and decrease of the particle size. Even though not directly correlated, the increase of the gel phase distribution coefficient, i.e. the increase of the available particle volume, would normally be accompanied by an increase of pore sizes as well. However, as mentioned above, McCue et al. (Journal of Chromatography A, 989 (2003) 139-153: "Evaluation of protein A chromatography media") suggested that decrease of the pore size increased dynamic binding capacity in the reported study. Thus, the substantial increase in dynamic binding capacity of the present separation matrix is contradictory to the teachings of the prior art, and was consequently quite unexpected.

Even though the most preferred format of the present separation matrix is particles, other formats are also encompassed by the invention such as a monolith; a filter or membrane; a chip, a surface, capillaries or the like.

In a second aspect, the present invention relates to a chromatography column comprising a separation matrix as defined above. The column may have been packed with the matrix according to conventional packing methods, or filled with matrix for operating in expanded bed mode. For expanded mode operation, the particles are preferable provided with a high density filler, as is well known in this field. In an advantageous embodiment, the column is made from any conventional material, such as a biocompatible plastic, e.g. polypropylene, stainless steel or glass. The column may be of a size suitable for laboratory scale or large-scale purification and/or detection of antibodies. In a specific embodiment, the column according to the invention is provided with luer adaptors, tubing connectors, and domed nuts.

The present invention also encompasses a kit for purification of antibodies, which kit comprises, in separate compartments, a chromatography column packed with a separation matrix as defined above, one or more buffers and written instructions for large-scale capture of antibodies from feed. In a specific embodiment, the present kit also comprises luer adaptors, tubing connectors, and domed nuts.

In a third aspect, the present invention relates to a method of purification of antibodies by affinity chromatography, which process comprises contacting a process feed with a separation matrix according to the invention to adsorb antibodies, an optional wash step of antibodies adsorbed to the separation matrix, adding an eluent that releases the antibodies from the separation matrix and recovery of antibodies from the eluate. Using the present method, dynamic binding capacities above 35 mg antibody/ml separation matrix, such as above 40 mg antibody/ml separation matrix, can be obtained. Thus, the dynamic binding capacity when carrying out the present method may be in the range of 35-50 mg antibody/ml separation matrix, such as 39-40 mg antibody/ml separation matrix.

The present method may be used to isolate antibodies from culture liquids and supernatants. In an advantageous embodiment, the process feed comprises fermentation broth. In this embodiment, the antibodies are purified from host cell proteins, DNA, viruses, endotoxins, nutrients, components of a cell culture medium, such as antifoam agents and antibiotics, and product-related impurities, such as misfolded species and aggregates. In a specific embodiment, the feed has been subjected to mechanical filtration before its contact with the separation matrix, and consequently the mobile phase is a clarified cell culture broth. Suitable conditions for adsorption are well known to those of skill in the art.

The present method is useful to purify any kind of monoclonal or polyclonal antibodies, such as antibodies originating from mammalian hosts, such as mice, rodents, primates and humans, or antibodies originating from cultured cells such as hybridomas. In one embodiment, the antibodies recovered are human or humanised antibodies. In another embodiment, the antibodies are selected from antibodies originating from the group that consists of mouse, rat, rabbit, hamster, guinea pig, cow, sheep, goat, pig, and chicken. The antibodies may be of any class, i.e. selected from the group that consists of IgA, IgD, IgE, IgG, and IgM. In one embodiment, the antibodies recovered are immunoglobulin G (IgG). In a specific embodiment, the IgGs are selected from the group that consists of human IgG1, human IgG2, human IgG4, human IgGA, human IgGD, human IgGE, human IgGM, mouse IgG1, mouse IgG2a, mouse IgG2b mouse IgG3, rabbit Ig, hamster Ig, guinea pig Ig, bovine Ig, and pig Ig, preferably human IgG1, human IgG2, human IgG4, mouse IgG2a, rabbit Ig, and guinea pig Ig. Thus, in on one embodiment, the antibodies are monoclonal antibodies. As is well known, monoclonal antibody technology involves fusion of immortal cells, having the ability to replicate continuously, with mammalian cells to produce an antibody. The resulting cell fusion or 'hybridoma' will subsequently produce monoclonal antibodies in cell culture. In this context, it is to be understood that the term "antibodies" also includes antibody fragments and any fusion protein that comprises an antibody or an antibody fragment. Thus, the present method is useful to isolate any immunoglobulin-like molecule, which presents the Protein A and/or Protein G and/or Protein L binding properties of an immunoglobulin.

The present method is operable as a conventional liquid chromatography process, wherein the mobile phases are passed through the separation matrix by impact of gravity and/or pumping. Thus, in one embodiment, the separation matrix is present in a chromatography column through which said process feed and eluent are passed.

In an alternative embodiment, this aspect of the invention relates to a method of purification of a liquid from one or more antibodies by affinity chromatography, which process comprises contacting a liquid with a separation matrix according to the invention to adsorb antibodies and recovering the purified liquid. This embodiment is e.g. useful in the case where the liquid is blood or blood plasma, from which it is desired to remove one or more antibodies to obtain a safe blood product. In one embodiment, the antibodies are released from the separation matrix by adding an eluent to prepare the separation matrix for re-use.

The adsorption and elution of antibodies according to the present invention are easily released by standard conditions, such as those recommended for similar commercial products, see e.g. MabSelect™ application notes (Amersham Biosciences, Uppsala, Sweden). Thus, the elution is e.g. gradient elution performed by adding an eluent of changing pH to the separation matrix.

In a last aspect, the present invention relates to a multi-step process for the purification of antibodies, which process comprises a capture step as described above followed by one or more subsequent steps for intermediate purification and/or polishing of the antibodies. In one embodiment, the capture step is followed by hydrophobic interaction and/or ion exchange chromatography. In an alternative step, the capture step is followed by multimodal anion or cation exchange chromatography. In a preferred embodiment of the present process, the capture step is carried out on MabSelect™ Xtra (Amersham Biosciences, Uppsala, Sweden).

EXAMPLES

The present examples are provided for illustrative purposes only, and should not be construed as limiting the scope of the present invention as defined by the appended claims. All references given below and elsewhere in the present specification are hereby included herein by reference.

Example 1

Separation Matrices

Agarose particles were prepared by suspension gelation as disclosed in U.S. Pat. No. 6,602,990 (Amersham Biosciences). More specifically, particles having a $K_{av}$ of 0.69 were produced by the appropriate adjustment of solids content, according to well known principles in this field. Further, by adjusting the speed and duration of stirring, the median particle diameter was controlled to 80 μm.

The particles described above were epoxi-activated and recombinant Protein A (rprotein A) was coupled to the particles via C-terminal, following well known procedures as described e.g. in Hermanson, Greg T., Mallia, A. Krishna, Smith, Paul K. Immobilized Affinity Ligand Techniques, p. 118. Academic Press. ISBN 0-12-342330-9. The rProtein A ligands were coupled to a ligand density of 7.3 mg/ml.

The comparative separation matrix was MabSelect™, obtained from Amersham Biosciences, which according to the product note presents a median particle size of the cumulative volume distribution of 85 μm.

Example 2

Dynamic Binding Capacity

The dynamic binding capacity (DBC) of the separation matrix prepared as described in Example 1 was tested as follows: Human polyclonal IgG was loaded, 1.0 mg/ml at neutral pH onto two columns packed with the product. The capacity is determined at 10% breakthrough, and the results are shown in FIG. 1.

Equipment

| Packing of columns | | |
|---|---|---|
| Columns (2) | XK16/20 | Amersham Biosciences |
| Packing reservoir | XK16/20 | Amersham Biosciences |
| Pump | 25 ml/minute, e.g. P-900 | Amersham Biosciences |
| Relief valve Pressure meter | 0.3 MPa | Amersham Biosciences |

Chromatography
ÄKTA™ Explorer 10 or ÄKTA FPLC™ (Amersham Biosciences) Spectrophotometer, double beam

| Chemicals | | | |
|---|---|---|---|
| Ethanol | 99.5% | Spectroph. | |
| Sodium Chloride | p a | | |
| Sodium Dihydrogen Phosph. | p a | Baker | M = 137.99 g/mol |
| Sodium Hydroxide | p a | Prolabo | M = 40.00 g/mol |
| Sodium Citrate | p a | Merck | M = 75.07 g/mol |
| Hydrochloric acid | p a | | |
| Gammanorm | 165 mg/ml | Octapharma | |

Solutions
Buffers

| | |
|---|---|
| Packing solution 1: | 20% (v/v) ethanol containing 0.25 M NaCl. |
| Packing solution 2: | 20% (v/v) ethanol. |
| Adsorption buffer: | 0.020 M $NaH_2PO_4$ containing 0.15 M NaCl adjusted to pH 7.4 ± 0.05 with a concentrated sodium hydroxide solution. |
| Desorption buffer: | 0.1 M sodium citrate adjusted to pH 3.0 ± 0.05 with hydrochloric acid. |

IgG Sample Solution

Prepare a 1.00±0.01 mg/ml sample solution by diluting Gammanorm with adsorption buffer. The concentration of the sample solution (after dilution 1+1) should be checked by measuring the absorbance spectrophotometrically at 280 nm. Calculate the correct concentration using 1.38 ml/mg*cm as absorptivity coefficient.

Packing of Columns
Pre-Treatment of the Gel

Wash 50 ml gel on a glass filter funnel with packing solution 1 for 5 minutes. Suck dry using vacuum for 5 minutes. Blend carefully and weigh two portions of 14.3 g into two beakers. Add ~25 ml of packing solution 1.

Packing

Mount the packing reservoir to the column with a connecting piece. Measure and mark desired bed height. Transfer quantitatively the gel and fill up with packing solution 1. Pack with 25 ml/minute with packing solution 2 for 5 minutes downward flow at a maximum pressure of 0.3 MPa. Mark the bed height during flow. Remove the packing reservoir, mount the top adaptor to the gel, and run a flow of 10 ml/minute for 5 minutes more. Adjust or repack if necessary to a bed height of 10.0±0.3 cm.

Procedure
Control of Column Packing

The packing of the columns are checked by injecting a solution of acetone through the columns and calculating the symmetry of the resulting peak. Prepare a solution of 100 mg acetone/ml adsorption buffer. Inject 50 μl of the acetone solution on the column at a flow rate of 5 ml/minute. The peak asymmetry factor is then evaluated using the ÄKTA system, or calculated according to the following description.

The peak asymmetry factor is calculated as the absolute value of B/A, where A and B are calculated as the retention volume at maximum peak height minus the retention volume at 10% peak height. The column is approved if the symmetry is in the interval of 0.80-1.60.

Determination of the Breakthrough Capacity

The analysis should be performed on two columns at controlled room temperature, 23±1° C. The breakthrough capacity is determined at a mobile phase velocity of 250 cm/hour. Check the flow rate according to section 6.3. Run adsorption buffer through the bypass position until a stable baseline is reached. Autozero, and apply 35 ml of IgG solution also through bypass to obtain a stable 100% signal. It is important that the flow is the same as during the analysis. After a stable baseline with adsorption buffer is reached again at bypass position, the column is equilibrated with 5 column volumes of adsorption buffer. Autozero, and apply 100 column volumes of IgG solution to the column at a mobile phase velocity of 250 cm/h (8.38 ml/minute).

Calibration

It is essential that the chromatographic system is thoroughly calibrated with respect to volume delivery. Calibrate regularly according to the manual for the instrument, and check the flow rate for the pump used for sample application before every analysis.

Evaluation

The dynamic binding capacity is evaluated at 10% breakthrough, $q_{10\%}$. UV absorbance is detected at 280 nm. The 100% UV signal ($A_{100\%}$) is determined and noted, as well as the UV signal ($A_{sub}$) corresponding to the subclass of IgG that does not bind (determined at 60 ml from sample application start). The column volume ($V_C$) and the concentration ($C_0$) of the sample feed (two decimals) are also used for the calculations.

Dynamic binding capacity is calculated as the amount of IgG loaded onto the column until the concentration of IgG in the column effluent is 10% of the IgG concentration in the feed. The loaded amount is corrected for the amount of IgG breaking through the column before the 10% breakthrough occurs.

$$q_{10\%} = \frac{C_0}{V_C}\left[V_{app} - V_{sys} - \int_{V_{sys}}^{V_{app}} \frac{A(V) - A_{sub}}{A_{100\%} - A_{sub}} * dv\right]$$

where $C_o$ is the feed concentration, $V_c$ is the column volume, $V_{app}$ is the volume applied until 10% breakthrough, $V_{sys}$ is the system dead volume (column dead volume not included), the integral gives the total amount of IgG present in the effluent from the column up to the moment of 10% breakthrough, $A(V)$ is the absorbance value at a given applied volume and $A_{sub}$ is the absorbance contribution from the non-binding IgG subclass. The difference in the dynamic capacities between the single columns should not exceed 1.2 mg/ml packed gel.

Precision

The relative standard deviations for the capacities are 2%.

REFERENCES

In "Handbook of Process Chromatography, A Guide to Optimization, Scale-Up and validation" (1997) Academic Press, San Diego. Gail Sofer & Lars Hagel eds. ISBN 0-12-654266-X, pp 308-310.

Example 3

Calculation of the Gel Phase Distribution Coefficient

Principle

The gel phase distribution coefficient of a particle according to example 1 is determined by gel filtration. Two dextrans with different sizes are run through a packed HR16/30 column. Retention volumes for each dextran are detected, and used to calculate $K_{av}$, a value describing the fraction of the particle volume available for a certain molecular weight. From the $K_{av}$-values the $K_{av}$-value for Mp 110000 is reported.

Equipment

| | Packing | |
|---|---|---|
| Column | HR 16/30 | |
| Packing tube | HR 16/30 | |
| Pump | ÄKTA ™ P-900 pump or equal | |

Selectivity Test

| ÄKTA explorer 10 System or equal | |
|---|---|
| Control | UNICORN ™ |
| Sample Injection | Autosampler A-900* |
| Sample loop | 200 µl |
| Pumps | P-900 |
| Detector | Shimadzu RI-detector |

Chemicals

Mobile phase for packing is distilled water and for the selectivity test 0.20 M NaCl in distilled water.

The column packing is tested with an injection of 2% acetone in a distilled water mobile phase.

The dextrans used in the selectivity test are:

| Native dextran | 5 mg/ml | Amersham Biosciences |
|---|---|---|
| Mp = 196300 | 10 mg/ml | Pharmacosmos |
| Mp = 66700 | 8 mg/ml | Pharmacosmos |

All dextrans are diluted in 0.20 M NaCl except for Mp=196300 which is diluted in 0.25 M NaCl, serving as a marker for the total volume of the column.

Safety Directions

No extra safety precautions need to be taken.

Sample Pre-Treatment

Wash the gel with 0.20 M NaCl on a glass filter, and dry until the gel starts cracking. 60 ml dry gel is then dissolved in 60 ml 0.20 M NaCl, forming a gel slurry.

Calibration

Control and calibrate the used instruments according to their individual manuals.

Procedure

One analysis consists of packing of one column that is tested twice i.e. each dextran is injected twice.

Column Packing

A HR16/30 column (Amersham Biosciences) is packed by the following method: Connect the column to a packing tube with a bottom adaptor, using a packing connector. Place the column in the column stand with the packing tube at the bottom. Connect the packing tube adaptor to the pump and pump a little to fill it with app. 0.5 cm water. Transfer the gel slurry and fill up with 0.2 M NaCl, place the filter and bottom adaptor on the column.

Apply a flow of 22 ml/min, turn the column right and continue pumping for 10 minutes. Remove excessive gel with a Pasteur pipette. Place the filter on top and screw on the top adaptor and adjust to the bed surface. Apply a flow of 10 ml/min until the bed is stable, adjust the adaptor again then apply the flow again to check the bed stability. If no further compression of the gel bed is observed it is considered stable.

Test the packing quality by injecting a 2% acetone solution (in distilled water). Equilibration before the injection is not necessary since the mobile phase is not changed. Elute the acetone at 150 cm/h (5 ml/min) during 1.2 CV. Calculate plate number and asymmetry factor from the resulting peak. Acceptance criteria: plate number >2400 N/m, asymmetry 0.7-1.3.

Calculation of the Number of Plates: N/L $$N = 5.54 * (t_R/W_h)^2$$

$t_R$=retention time $W_h$=peak–width at half height $L$=column height (m)

Measure the asymmetry factor at 10% of peak height.

Selectivity Test

After acceptance of the packing criteria, the selectivity method can be run including the following steps:
1. Column equilibration, at least 1.5 CV 0.20 M NaCl.
2. Dextran injection of 200 µl with the A-900 auto sampler.
3. Elution with 1.3 CV of the mobile phase.
Step 2 and 3 are then repeated for each dextran or dextran mix*.

*The dextrans can be mixed according to the following protocol, but can also be injected one at a time.

Mix 1: native dextran+Mp 66700
Mix 2: Mp 196300 in 0.25M NaCl

Sources of Error

Air trapped in the pump can give wrong flow velocity, it is therefore important to control that the pressure has been stable during the run.

Evaluation

The retention volume for each dextran is extracted from the RI curve in the resulting chromatogram, where a peak is defined as RI-maximum for the dextran in question. $K_{av}$ for the dextrans are then calculated from formula:

$$K_{av} = (V_R - V_o)/(V_c - V_o)$$

where
$V_R$=retention volume for the eluted dextran adjusted for the extra column volume, ml
$V_o$=interstitial volume (the retention volume for native dextran) adjusted for the extra column volume (ml)
$V_c$=geometric volume of the column (bed height, cm·surface area of column, cm$^2$)
$K_{av}$-values are then plotted against log Mp of the dextrans. Two values from each dextran results in four values plotted in one diagram. A linear interpolation between the two dextrans gives the
$K_{av}$-value corresponding to the molecular mass of 110000 (Mp-value) which is reported.

All patents, patent publications, and other published references mentioned herein are hereby incorporated by reference in their entireties as if each had been individually and specifically incorporated by reference herein. While preferred illustrative embodiments of the present invention are described, one skilled in the art will appreciate that the present invention can be practiced by other than the described embodiments, which are presented for purposes of illustration only and not by way of limitation. The present invention is limited only by the claims that follow.

What is claimed is:

1. A separation matrix comprising porous cross-linked agarose gel particles and antibody-binding protein ligands immobilised thereon via cysteine using epoxy coupling, wherein the ligand density is in the range of 5.0-10 mg/ml; the median particle diameter is in the range of 65-84 µm; said matrix provides a dynamic binding capacity above 40 mg antibody/ml separation matrix at 2.4 minutes residence time; and the gel phase distribution coefficient ($K_{av}$) is between 0.65 and 0.85 when measured using a dextran substrate of 110 kDa by gel filtration on said porous cross-linked agarose gel particles.

2. The separation matrix of claim 1, wherein said ligand density is in the range of 5.5-9.0 mg/ml.

3. The separation matrix of claim 1, wherein said median particle diameter is about 75 µm.

4. The separation matrix of claim 1, wherein said agarose polymers have been allylated before gelation.

5. The separation matrix of claim 1, wherein said ligands comprise Fc-binding protein.

6. The separation matrix of claim 5, wherein said Fc-binding protein is Protein A.

7. The separation matrix of claim 6, wherein said Protein A is recombinant Protein A produced in a non-mammalian source.

8. The separation matrix of claim 1, wherein the ligands comprise a monomer, dimer or multimer of Protein A domains.

9. The separation matrix of claim 8, wherein one or more of said Protein A domains have been mutated.

10. A chromatography column comprising the separation matrix of claim 1.

11. A kit for large-scale capture of antibodies from feed, which kit comprises, in separate compartments, a chromatography column packed with the separation matrix of claim 1, one or more buffers and written instructions for its use.

12. A method of purification of antibodies by affinity chromatography, which process comprises contacting a process feed with the separation matrix of claim 1 to adsorb antibodies, an optional wash step of antibodies adsorbed to the separation matrix, adding an eluent that releases the antibodies from the separation matrix and recovery of antibodies from the eluate.

13. The method of claim 12, wherein said process feed comprises fermentation broth.

14. The method of claim 12, wherein said feed has been subjected to mechanical filtration before its contact with the separation matrix.

15. The method of claim 12, wherein said antibodies are monoclonal antibodies.

16. The method of claim 12, wherein said separation matrix is present in a chromatography column through which said process feed and eluent are passed.

17. A method of purification of a liquid from one or more antibodies by affinity chromatography, which process comprises contacting said liquid with the separation matrix of claim 1 to adsorb said antibodies and recovering the purified liquid.

18. The method of claim 17, wherein said antibodies are released from said separation matrix by adding an eluent to prepare said separation matrix for re-use.

19. A multi-step process for the purification of antibodies, which process comprises the capture step of claim 17 followed by one or more subsequent steps for intermediate purification and/or polishing of the antibodies.

20. The process of claim 19, wherein said capture step is followed by hydrophobic interaction and/or ion exchange chromatography.

21. The process of claim 19, wherein said capture step is followed by multimodal anion or cation exchange chromatography.

* * * * *